(12) United States Patent
Yu et al.

(10) Patent No.: US 12,721,711 B2
(45) Date of Patent: Sep. 1, 2026

(54) ORAL CAVITY RESTORATION SPACE MEASURING DEVICE AND METHOD

(71) Applicant: SICHUAN UNIVERSITY, Chengdu (CN)

(72) Inventors: Haiyang Yu, Chengdu (CN); Qin Wu, Chengdu (CN); Chenyang Xie, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 434 days.

(21) Appl. No.: 18/270,489

(22) PCT Filed: Nov. 29, 2021

(86) PCT No.: PCT/CN2021/133860

§ 371 (c)(1),
(2) Date: Jun. 30, 2023

(87) PCT Pub. No.: WO2022/148177

PCT Pub. Date: Jul. 14, 2022

(65) Prior Publication Data

US 2024/0058111 A1 Feb. 22, 2024

(30) Foreign Application Priority Data

Jan. 8, 2021 (CN) ........................ 202110022657.8

(51) Int. Cl.
*A61C 19/04* (2006.01)
*A61B 1/24* (2006.01)

(52) U.S. Cl.
CPC ................ *A61C 19/04* (2013.01); *A61B 1/24* (2013.01)

(58) Field of Classification Search
CPC ......... A61C 19/04; A61B 1/24; A61B 5/1076; A61B 5/107
See application file for complete search history.

(56) References Cited

U.S. PATENT DOCUMENTS

| | | | | |
|---|---|---|---|---|
| 2020/0155285 | A1* | 5/2020 | Pesach | A61C 17/022 |
| 2021/0045850 | A1* | 2/2021 | Yu | A61C 8/0089 |
| 2024/0058111 | A1* | 2/2024 | Yu | A61B 1/24 |

FOREIGN PATENT DOCUMENTS

| | | | | |
|---|---|---|---|---|
| AU | 2010271158 A1 * | 2/2012 | | A61C 19/04 |
| CN | 2078612 U * | 6/1991 | | A61C 19/04 |
| CN | 2131485 Y * | 5/1993 | | A61C 19/04 |
| CN | 202113183 U * | 1/2012 | | |

(Continued)

OTHER PUBLICATIONS

CN 110881979 A, English translation (Year: 2025).*

(Continued)

*Primary Examiner* — Jeffrey G. Hoekstra

(57) ABSTRACT

The present disclosure discloses an oral cavity restoration space measuring device and method, wherein a depth measuring rod and a main scale are configured to be rigidly connected to each other; a gripping end and a measuring end are connected at a certain angle to reduce a measuring dead angle; a first detachable measuring claw and a second detachable measuring claw are used, and measurements of depth, width and length are integrated; and a digital display meter can rotate around the axis of a connecting rod so as to facilitate the viewing of displayed measurement data.

8 Claims, 9 Drawing Sheets

(56) References Cited

FOREIGN PATENT DOCUMENTS

| | | | | |
|---|---|---|---|---|
| CN | 204520697 U | | 8/2015 | |
| CN | 105796203 A | | 7/2016 | |
| CN | 205849573 U | * | 1/2017 | |
| CN | 108553185 A | | 9/2018 | |
| CN | 110881979 A | | 3/2020 | |
| CN | 210330776 U | | 4/2020 | |
| CN | 111759499 A | * | 10/2020 | ............. A61C 19/04 |
| CN | 213758697 U | | 7/2021 | |

OTHER PUBLICATIONS

International Search Report of PCT Patent Application No. PCT/CN2021/133860 issued on Jan. 28, 2022.

Yimin Zhao et al., Prosthodontics, Aug. 2020, pp. 43-45, 52-53, 63-64 and 81, Eighth Edition, People's Medical Publishing House.

* cited by examiner

ORAL CAVITY RESTORATION SPACE MEASURING DEVICE AND METHOD

TECHNICAL FIELD

The present disclosure relates to an oral medical instrument technology field, and more particularly to an oral cavity restoration space measuring device and method.

BACKGROUND

For a long time, a lot of data used to determine the treatment scheme and evaluate the treatment outcome exists in the diagnosis and treatment activities of stomatology, especially in the field of prosthodontics, the most typical data is the dimension of the oral cavity restoration space which can be prepared on the teeth to be repaired, different dimensions directly determine different treatment schemes and affect the prognosis. The following table lists relationships of several commonly used restoration schemes and corresponding dimensions of oral cavity restoration spaces (extracted from the eighth edition of prosthodontics, edited by Zhao Yimin, People's Medical Publishing House).

| | restoration space (mm) | | | |
|---|---|---|---|---|
| restoration scheme | occlusal surface/ incisal edge | (labial) buccal/ lingual surface | proximal surface | cervical margin |
| full metal crown | 0.8-1.5 | — | — | 0.35-0.8 |
| porcelain fused to metal crown | 1.5-2.0 | 1.2-1.5 or 0.8-1.5 | 1.8-2.0 | 0.3-1.0 |
| full ceramic crown | 1.5-2.0 | 1.0-1.5 | 1.0 | 0.8-1.0 |
| porcelain veneers | — | 0.3-0.5 | — | — |

These numerical values of the oral cavity restoration space need to be accurately mastered in the clinical diagnosis and treatment. Too high or too low of the numerical value, even an error of 0.1 mm may affect the health of the abutment teeth or the performance of the prosthesis and therefore affect the final restorative effect. In recent years, with the advent of the digital era, as well as the application of a large amount of new technologies and materials in the stomatology field, stomatology has developed towards the direction of digitalization, precision and minimally invasive, especially in the context of the maturity of target restorative space theory, the popularization of tooth preparation guide plate technology and the continuous strengthening of digital minimally invasive aesthetic restoration concept in the whole industry, higher accurate requirements on the data required by diagnosis and treatment of stomatology are put forward.

SUMMARY

The technical problems in the prior art are as follows:

Due to the narrow oral cavity space and the existence of different degrees and ranges of vision obscuration, traditional devices can't reach or be observed, especially in the measurement of the posterior region and the lingual side of the anterior region, resulting in the measurement failure. In addition, the functions of the currently used oral cavity measurement devices are fragmented, and one device can only measure distances in one specific direction.

For the technical problems mentioned above, the present disclosure provides an oral cavity restoration space measuring device and method, which can solve the problem of difficult measurement caused by the narrow oral cavity space.

The specific technical scheme is as follows:

an oral cavity restoration space measuring device, characterized in that, the device comprises: a shell, wherein the shell comprises a combined section, the combined section comprises a transverse section and a longitudinal section, one end of the transverse section is a measuring end capable of extending into the oral cavity, and the longitudinal section and the transverse section are connected at an included angle.

When using the measuring device in the prior art to measure the oral cavity restoration space, due to the narrow oral cavity space and the high difficulty of measurement, small errors may affect the follow-up treatment, and many positions in the oral cavity space may have problems of difficulty in data reading and unable measurement due to different degrees of vision obscuration, which may lead to large errors; in the present scheme, the shell of the device comprises the transverse section and the longitudinal section, which are connected at an included angle, and one end of the transverse section is regarded as the measuring end. Compared with the straight measuring device in the prior art, the present disclosure can more flexibly adjust the position of the measuring end in the oral cavity space, thus improving the flexibility of the measurement, greatly reducing the difficulty of the measurement and facilitating the operation, thus making a great contribution to the measurement of the oral cavity restoration space.

Moreover, the present scheme does not directly observe the scale with the naked eyes for reading, therefore the problem of inaccurate measurement caused by the vision occlusion during measurement does not exist.

It should be noted that the longitudinal section can be regarded as a gripping end, and the included angle between the transverse section and the longitudinal section should facilitate to extend the measuring end into the oral cavity space, and the value of the included angle between the transverse section and the longitudinal section should not be limited to one value. The included angle between the transverse section and the longitudinal section can also be set to be adjustable, which can also achieve the purpose of this disclosure.

In some possible examples, the device further comprises a third shell, wherein one end of the longitudinal section of the combination section away from the transverse section is connected with the third shell, and the longitudinal section is coaxial with the third shell.

The third shell can also be regarded as a part of the gripping end.

In some possible examples, the longitudinal section is perpendicular to the transverse section.

When measuring the oral cavity space, the longitudinal section is perpendicular to the transverse section, it is more convenient to observe the measured value of the oral cavity restoration space, and more convenient to operate when the measuring end of the transverse section extends into the oral cavity.

In some possible examples, the combination section and the third shell are both cavity structures, an interior of the transverse section is provided with a depth measuring rod capable of extending to an outer space of the measuring end, and an interior of the longitudinal section is provided with a transmission rod.

The device further comprises a gear disposed at a connection position between the transverse section and the longitudinal section, wherein the depth measuring rod and the transmission rod are capable of being engaged with the gear. The transmission rod is slidable along an axis of the third shell and drive the gear, realizing the slide of the depth measuring rod slide in the transverse section under the driving of the gear.

It should be noted that the transmission rod and the first rack both engage with the gear, and the transmission rod and the first rack engage two sides of the gear respectively. The thickness of the gear is not limited to a value equal to the sum of the thicknesses of the first rack and the thickness of transmission rod, as long as the transmission rod can drive the gear to rotate and therefore drive the first rack to move when the transmission rod moves.

In some possible examples, the device further comprises a connecting rod located inside the longitudinal section and the third shell, one end of the connecting rod is connected with one end of the transmission rod, and the other end of the connecting rod is connected with a main scale; by pushing or pulling the main scale, the connecting rod slides inside the longitudinal section and the third shell along the axis.

In some possible examples, an outer part of the main scale is sleeved with a digital display meter used for displaying measured data of the oral cavity restoration space, and the digital display meter is fixedly connected with the third shell.

It should be noted that the precision of the digital display meter reaches 0.01 mm.

At present, there is a lack of high-precision special measuring devices in the clinical diagnosis and treatment work of stomatology. In the measurement in the diagnosis and treatment of the oral cavity, especially in the distance measurement of small space, the phenomenon that the measurement beyond the measurement precision and measurement range of the device often exists. For example, in the commonly used method of measuring the space for tooth preparation with a periodontal probe, because the measurement precision of this device is only 0.5 mm, if the true value of a distance is not an integral multiple of 0.5 mm, for example, the actual distance of prepared restoration space is 0.8, 1.2 or 1.8 mm listed in the table above, the results measured with this device must contain estimation, rather than objective and true values. Therefore, in essence, using this device to measure can only be a qualitative estimation, rather than a measurement of the actual space distance, that is, the measurement using this device is not an actual measurement of an objective structure. It can be seen that the current diagnosis and treatment for oral cavity restoration in small space is still in a way of qualitative judgment based on subjective experience, rather than in a way of quantitative and objective judgment and treatment based on accurate data. That is, different measurers may get different values for the same structure, and finally make different or even opposite therapeutic schedule. The main reason for this situation is the lack of a high-precision measuring device in the face of oral cavity which is of complex structure and narrow space, especially the teeth which are irregular and in small sizes exist therein.

Therefore, the digital display meter in the present scheme can directly show the measured value on the display screen by measuring the relative position of the main scale in the digital display meter. Compared with observing the scale line with the naked eye, the disclosure completely avoids the problem of non-objective measurement data due to personal subjective judgment and completely eliminates problem of inaccurate reading caused by the effect of light on the visual acuity of the measurer.

In the prior art, the method of measuring distance using high-accuracy three-dimensional imaging technology has hysteresis and cannot measure distance quickly in real time, and the equipment required by this method is expensive and the operation is very complex. Moreover, as an indirect measuring method, its accuracy is directly affected by the accuracy of the three-dimensional reconstruction model.

Therefore, the digital display meter adopted in this scheme directly displays the measured data of the oral cavity restoration space, greatly improving the accuracy, objectivity, scientificity and safety of oral diagnosis and treatment in the field.

In some possible examples, the main scale is rotatable around an axis of the connecting rod.

The main scale can rotate around the axis of the connecting rod, the digital display meter sleeved on the main scale can rotate synchronously with the main scale, and the third shell fixedly connected with the digital display meter can also rotate. It should be noted that the third shell can rotate around the axis of the longitudinal section but will not detach from the end of the longitudinal section away from the transverse section. In this disclosure, when measuring the oral cavity restoration space, the digital display meter can be rotated to make the display screen of the digital display meter in a position convenient for the measurer's observation.

In some possible examples, the depth measuring rod comprises a first rack and a measuring head; a side wall of one end of the first rack is provided with a retaining rod, wherein the retaining rod extends out of the transverse section and is slidable in a hollow of the transverse section; the measuring head is connected at the other end of the first rack away from the retaining rod, the measuring head can be extended and retracted along with the first rack, and the measuring head can be extended out of the transverse section and retracted into the interior of the transverse section.

When the measurement is completed or the operation is reset, the gear can be driven by shifting the retaining rod. When the first rack slides towards the side away from the measurement end, the gear drives the transmission rod to slide towards the position of the main scale, making the main scale return to the original position, which facilitates the next measurement; it should be noted that the main scale can also be returned to the original position by pulling the main scale, and the measuring head can be exactly retraced into the transverse section following the movement of the first rack.

In some possible examples, the device further comprises a measuring assembly for performing dimension measurement, the measuring assembly comprises a first measuring claw and a second measuring claw, the first measuring claw is detachably connected at an end portion of the depth measuring rod extending out of the transverse section, the second measuring claw is detachably connected at an outer sidewall of the end of the transverse section and a measuring gap is formed between the first measuring claw and the second measuring claw.

When the first measuring claw and the second measuring claw are installed, the width and length of the oral cavity restoration space can be measured; when the first measuring claw and the second measuring claw are removed, the depth of the oral cavity restoration space can be measured.

The present disclosure also provides an oral cavity restoration space measuring method to measure the length and width of the oral anatomical structure by using the oral cavity restoration space measuring device, the method comprises following steps:

pushing or pulling the main scale, wherein the main scale drives the transmission rod in the longitudinal section to rotate the gear, and the gear drives the measuring head of the depth measuring rod to move, realizing the extending and retracting of the measuring head inside the transverse section;

the transmission rod drives the gear to rotate and the gear drives the first rack to move, so as to transform the direction of movement from a direction along an axis of the longitudinal section to a direction perpendicular to the axis of the longitudinal section; and locking the position of the main scale in the digital display meter, and then rotating the digital display meter along an axis direction of the main scale, so that the data on the digital display meter is convenient to observe.

Compared with the prior art, the present disclosure has the following advantages and beneficial effects:

In this disclosure, the depth measuring rod and the main scale are rigidly connected, and are driven in the form of gear and rack engaging. This connection structure not only has high precision, but also enables the gripping end and the measuring end to be connected in a certain angle rather than in a straight line, so as to realize the measurement of some parts in the narrow oral cavity space which cannot be reached by the traditional oral measuring scale, reducing measuring dead angles.

BRIEF DESCRIPTION OF THE DRAWINGS

The figures described herein are used to provide a further understanding of the embodiments of the present disclosure and constitute a part of the present application but without limiting the embodiments of the present disclosure. In the figures.

DETAILED DESCRIPTION OF THE PREFERRED EMBODIMENTS

The oral cavity restoration space measuring device and method of this disclosure will be described in detail below in combination with the attached drawings of the specification.

Embodiment 1

As shown in FIGS. 1 to 18, the oral cavity restoration space measuring device comprises a shell, the shell comprises a combination section 78, the combination section 78 comprises a transverse section 80 and a longitudinal section 79, one end of the transverse section 80 is a measuring end capable of extending into the oral cavity space, and the longitudinal section 79 and the transverse section 80 are connected at an included angle.

It should be noted that the longitudinal section 79 can be regarded as the gripping end, the included angle between the transverse section 80 and the longitudinal section 79 should facilitate to extend the measuring end into the oral cavity space, and the value of the included angle between the transverse section 80 and the longitudinal section 79 is not limited to one value, and the included angle between the transverse section 80 and the longitudinal section 79 can also be arranged to be adjustable, which can also realize the purpose of this disclosure.

Embodiment 2

Figure 1:
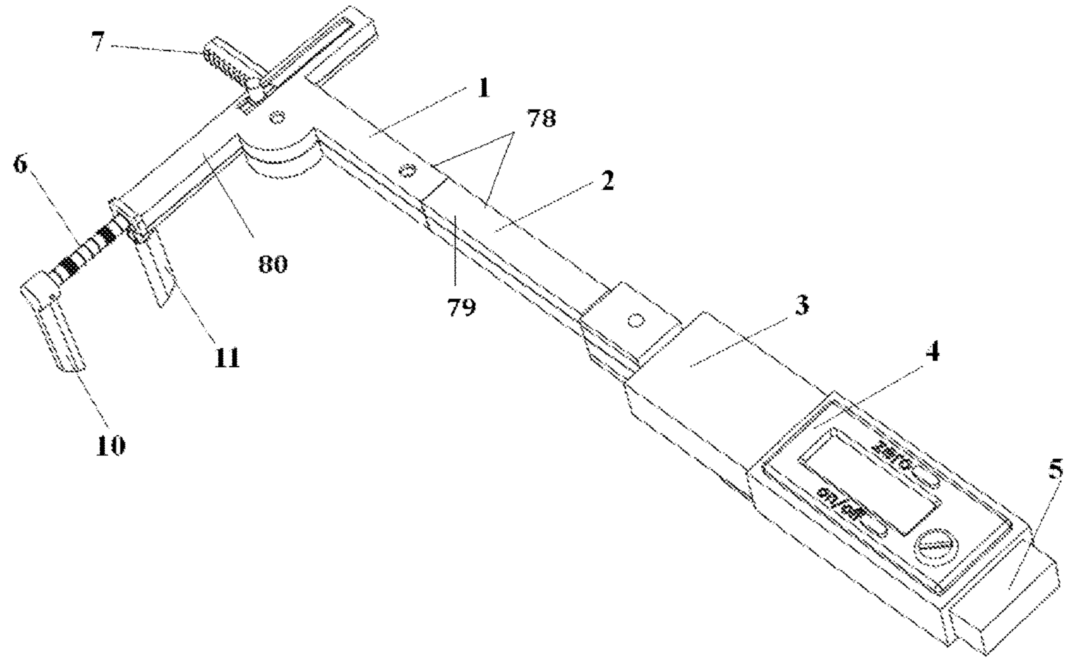
FIG. 1 is a schematic diagram of the overall structure of the present disclosure.
Figure 2:
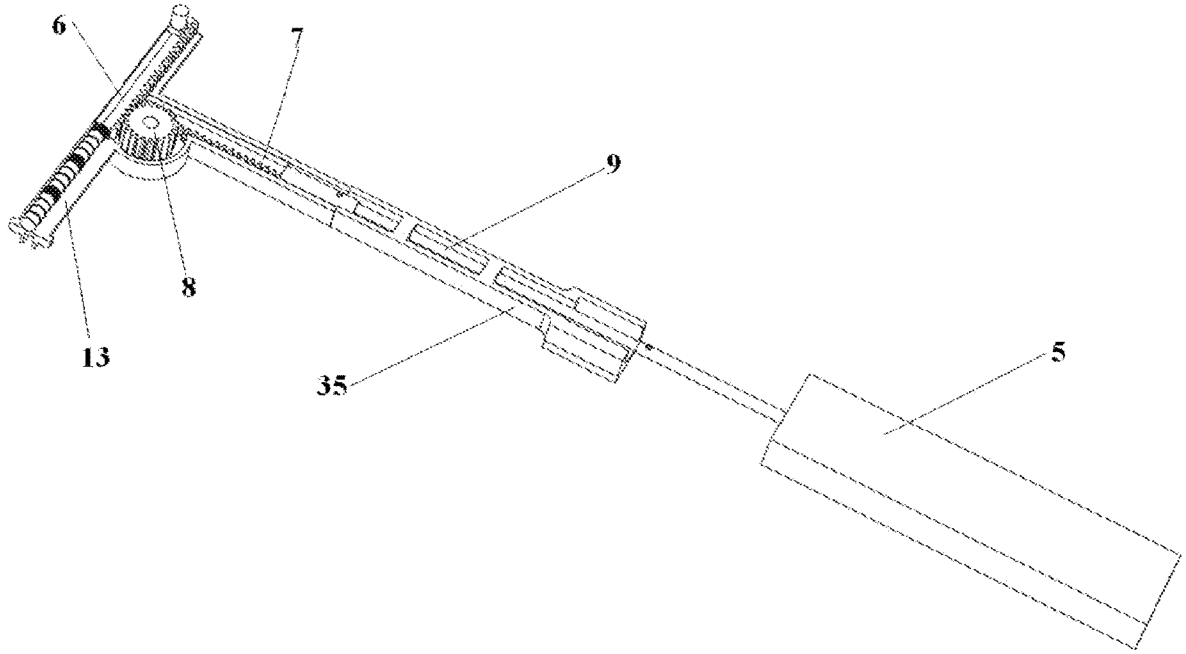
FIG. 2 is a schematic diagram of the internal structure in non-working state.
Figure 3:
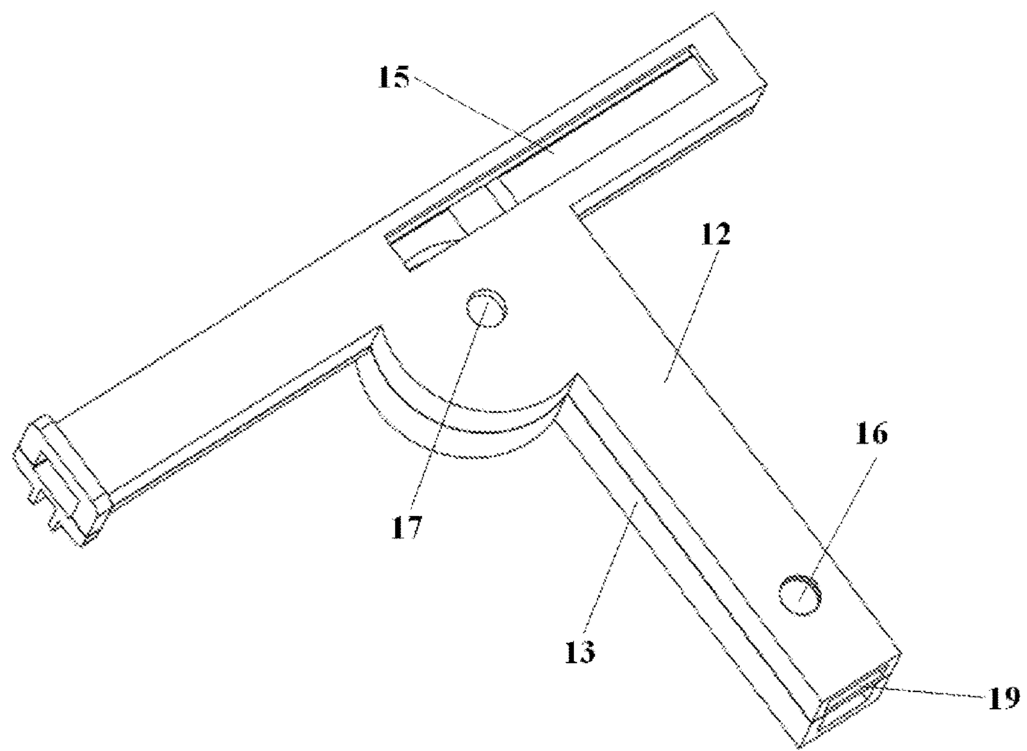
FIG. 3 is a schematic diagram of the first shell.
Figure 4:
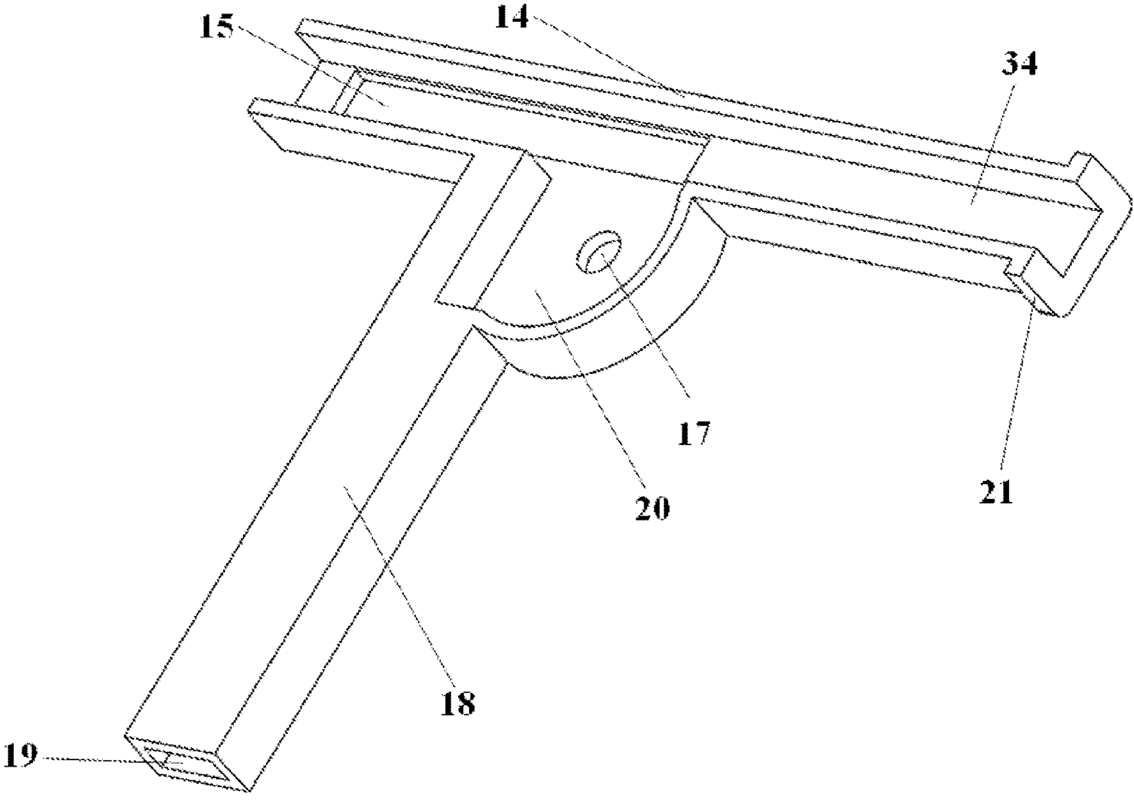
FIG. 4 is a schematic diagram of the internal structure of the first cover body.
Figure 5:
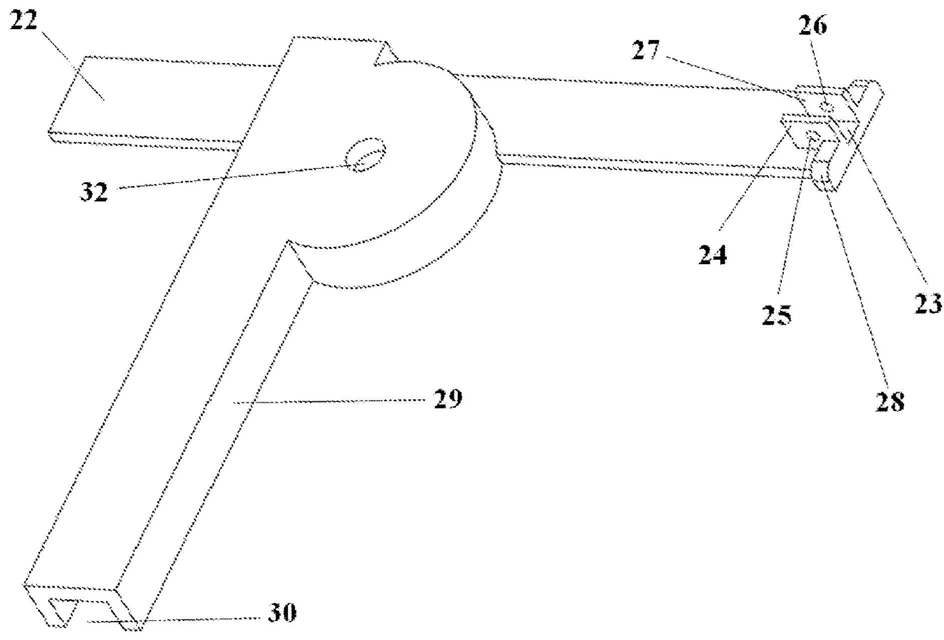
FIG. 5 is a schematic diagram of the external structure of the second cover body.
Figure 6:
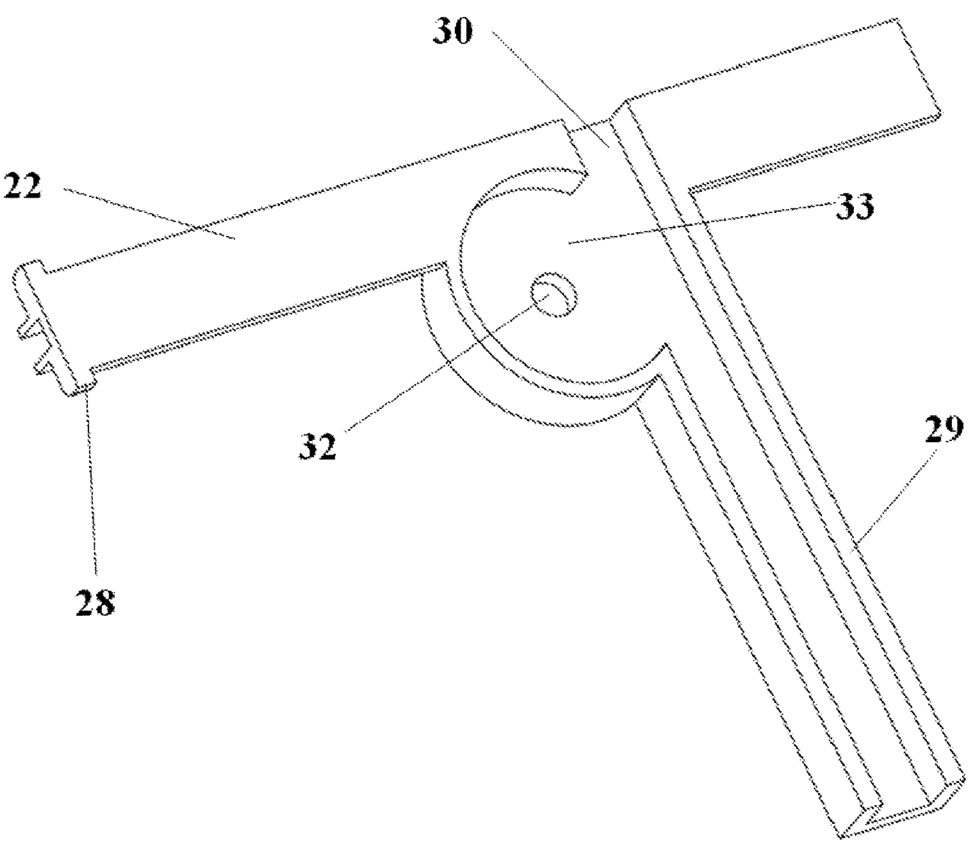
FIG. 6 is a schematic diagram of the internal structure of the second cover body.

This embodiment is a further improvement of embodiment 1:

As shown in FIG. 1 and FIG. 2, the device comprises the first shell 1, the second shell 2, the third shell 3, the digital display meter 4, the main scale 5, the depth measuring rod 6, the transmission rod 7, the gear 8, the transmission rod 7, the first measuring claw 10, and the second measuring claw 11. The second shell 2 is inserted in the first shell 1 and then fixed with screws. The third shell 3 is inserted in the second shell 2 and then connected to the second shell 2 by screws, and the third shell 3 can rotate around the connecting rod 9 without detaching from the second shell 2. The depth measuring rod 6 and the transmission rod 7 are engaged with the gear 8 and installed in the first shell 1, and the angle formed between the depth measuring rod 6 and the transmission rod 7 is a right angle. The gear 8 is connected with the first shell 1 through a shaft; after the connecting rod 9 passes through the second shell 2 and the third shell 3, one end of the connecting rod 9 is inserted in the transmission rod 7 and fixed by screws, and the other end of the connecting rod 9 is inserted in the main scale 5, and the connecting rod 9 and the main scale 5 are connected by screws, and the main scale 5 can rotate around the connecting rod 9. After the digital display meter 4 is sleeved on the main scale 5, the digital display meter 4 and the third shell 3 are fixed by screws. The first measuring claw 10 and the second measuring claw 11 are used when measurement for width or length is required. The first measuring claw 10 and the depth measuring rod 6 are fixed through screws after the first measuring claw 10 is installed on and located at the exact position of the depth measuring rod 6. The second measuring claw 11 and the first shell 1 are fixed through screws after the second measuring claw 11 is installed on the first shell 1.

As shown in FIGS. 3, 4, 5 and 6, the first shell 1 consists of the first cover body 12 and the second cover body 13. The first cover body 12 and the second cover body 13 are fixed with screws or buckles after butting, forming a T-shaped whole structure. The interior of the first cover body 12 is provided with a first groove 34 along the long axis direction of the transverse section of the first cover body 14, and the bottom wall of the first groove 34 is provided with a hollow 15 which is rectangular in shape. The front part of the transverse section of the first cover body 14 is provided with a first edge 21 which is protruding outward. The outer surface of the lower part of the longitudinal section of the first cover body 18 is provided with a first threaded hole 16, and the bottom of the longitudinal section of the first cover body 18 is provided with a first notch 19 which is rectangular in shape, and the first notch 19 is communicated with the first threaded hole 16. The interior of the first cover body 12 is provided with a first sector-shaped space 20, and a first shaft hole 17 is disposed at the center of the circle of the first sector-shaped space 20. The front part of the transverse section of the second cover body 22 is provided with a second edge 28 which is protruding outward, the middle portion of the second edge 28 is provided with a second notch 23, the first side wall 24 of the second notch 23 is provided with a sixth threaded hole 25, the second side wall 27 of the second notch 23 is provided with a seventh threaded hole 26. The interior of the second cover body 13 is provided with a second groove 30 along the long axis of the longitudinal section of the second cover body 29, the interior of the second cover body 13 is provided with a second sector-shaped space 33, and a second shaft hole 32 is disposed at the center of the second sector-shaped space 33.

Figure 7:
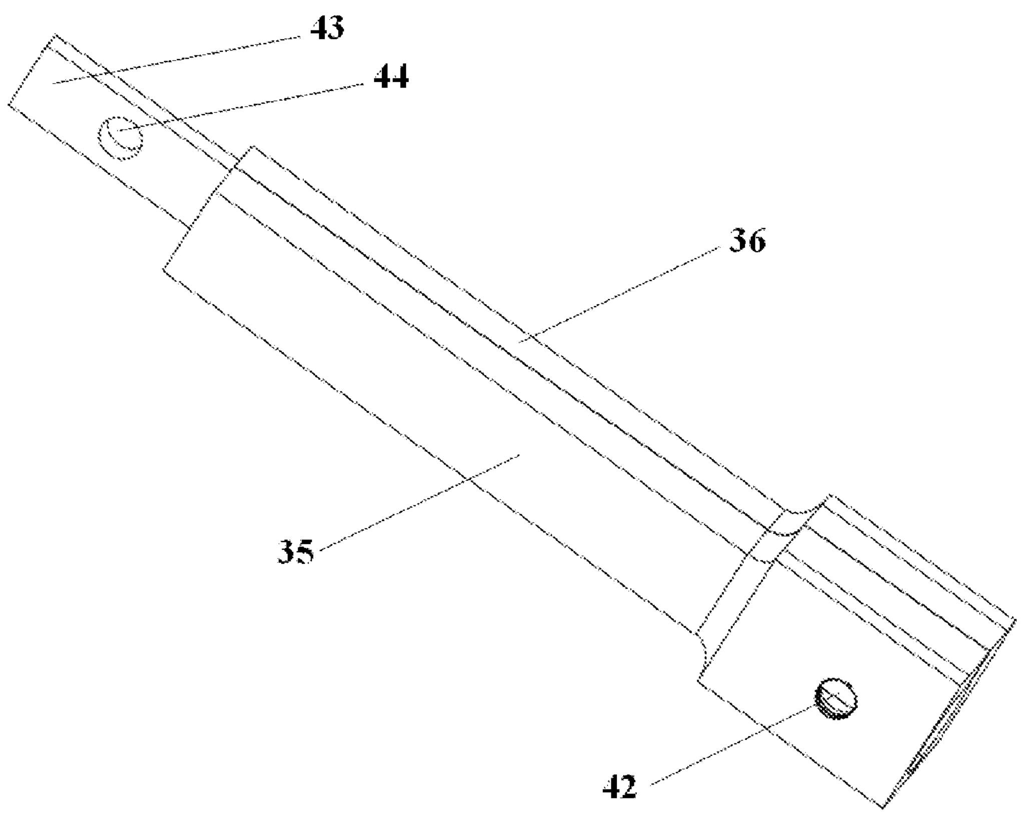
FIG. 7 is a schematic diagram of the second shell.
Figure 8:
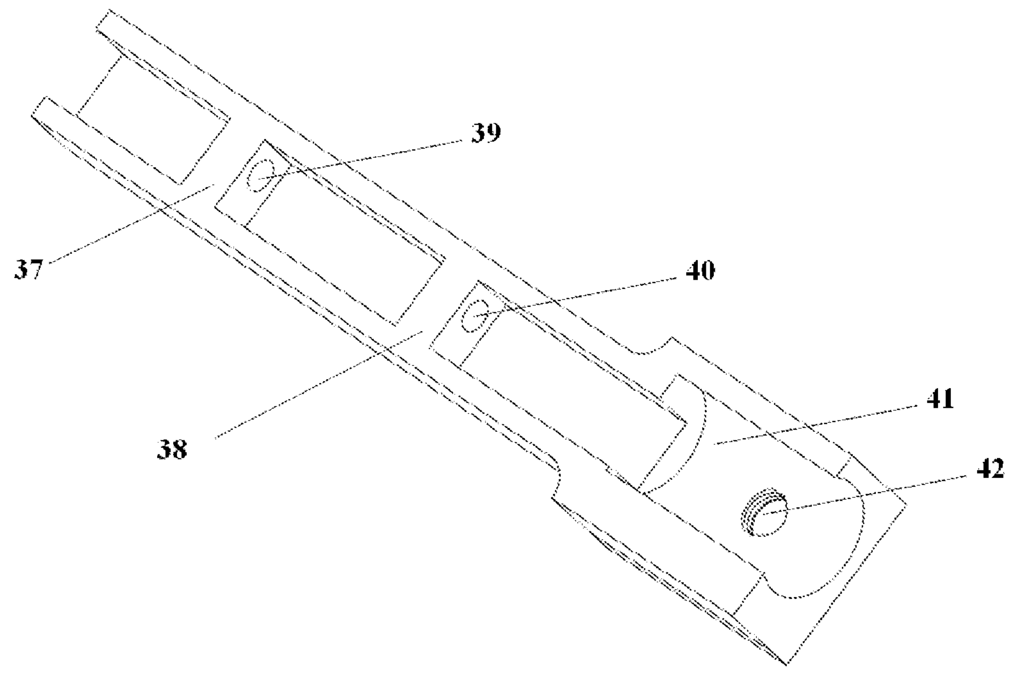
FIG. 8 is a schematic diagram of the interior of the third shell.
Figures 9, 10:
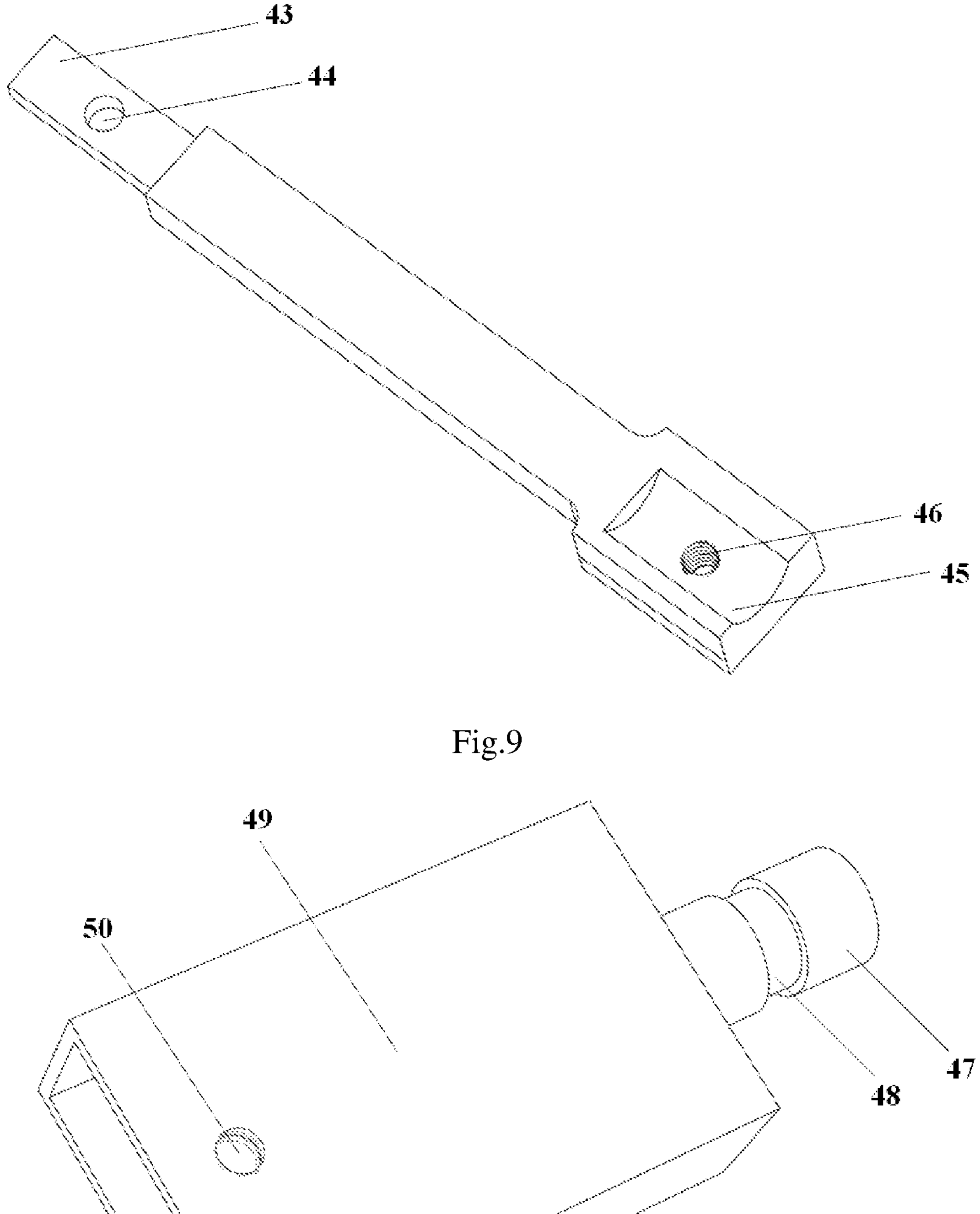
FIG. 9 is a schematic diagram of the interior of the fourth shell.
FIG. 10 is a schematic diagram of the third shell.

As shown in FIGS. 7, 8 and 9, the second shell 2 consists of a third cover body 35 and a fourth cover body 36. The third cover body 35 and the fourth cover body 36 are fixed with screws or buckles after butting. The interior of the third shell 3 is provided with, from top to bottom, a first bracket 37 of the connecting rod 9, a second bracket 38 of the connecting rod 9 and a first semi-cylindrical space 41. The center of the first bracket 37 of the connecting rod 9 is provided with a fifth through hole 39, the center of the second bracket 38 of the connecting rod 9 is provided with a sixth through hole 40, the side wall of the first semi-cylindrical space 41 is provided with a second threaded hole 42, and the front part of the fourth cover body 36 is provided with a plug 43, the center of the plug 43 is provided with a seventh through hole 71, the interior of the fourth cover body 36 is provided with a second semi-cylindrical space 45, the side wall of the second semi-cylindrical space 45 is provided with a third threaded hole 46, the second threaded hole 42 and the third threaded hole 46 are equal in diameter and have a coaxial relationship after the third cover body 35 and the fourth cover body 36 form the second shell 2.

As shown in FIG. 10, the third shell 3 is integrally formed, and the front part of the third shell 3 is provided with a tubular protruding part 47, and the middle of the outer wall of the tubular protruding part 47 is provided with a first annular groove 48. The width of the first annular groove 48 is equal to the diameter of the second threaded hole 42. The rear part of the third shell 3 is a structure in a shape of a square tubular referred as the fifth shell 49, and one side wall of the fifth shell 49 is provided with a fourth threaded hole 50.

Figure 11:
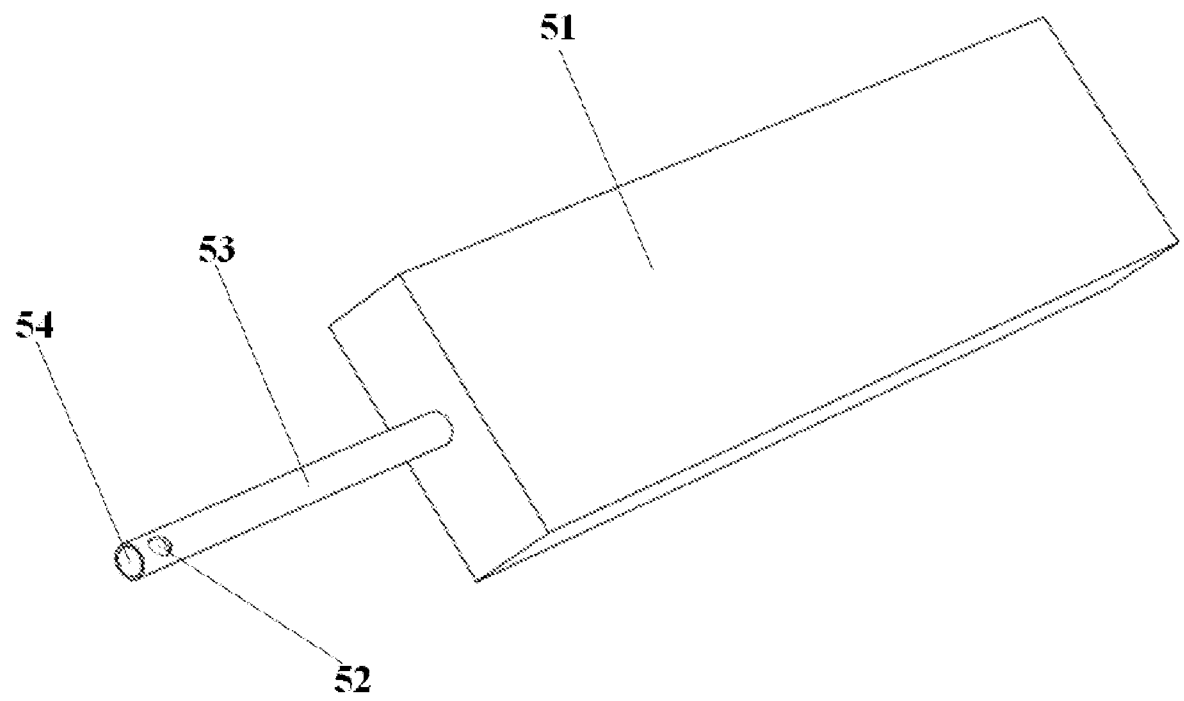
FIG. 11 is a schematic diagram of the main scale.

As shown in FIG. 11, the main scale 5 consists of a ruler body 51 and a ruler rod 53, the ruler body 51 is rectangular in shape, the front end of the ruler rod 53 is cylindrical in shape. The ruler rod 53 is provided with an eighth threaded hole 52. The second blind tube 54 and the eighth threaded hole 52 on the ruler rod 53 are communicated with each other, and the second blind tube 54 is coaxial with the ruler rod 53.

Figure 12:
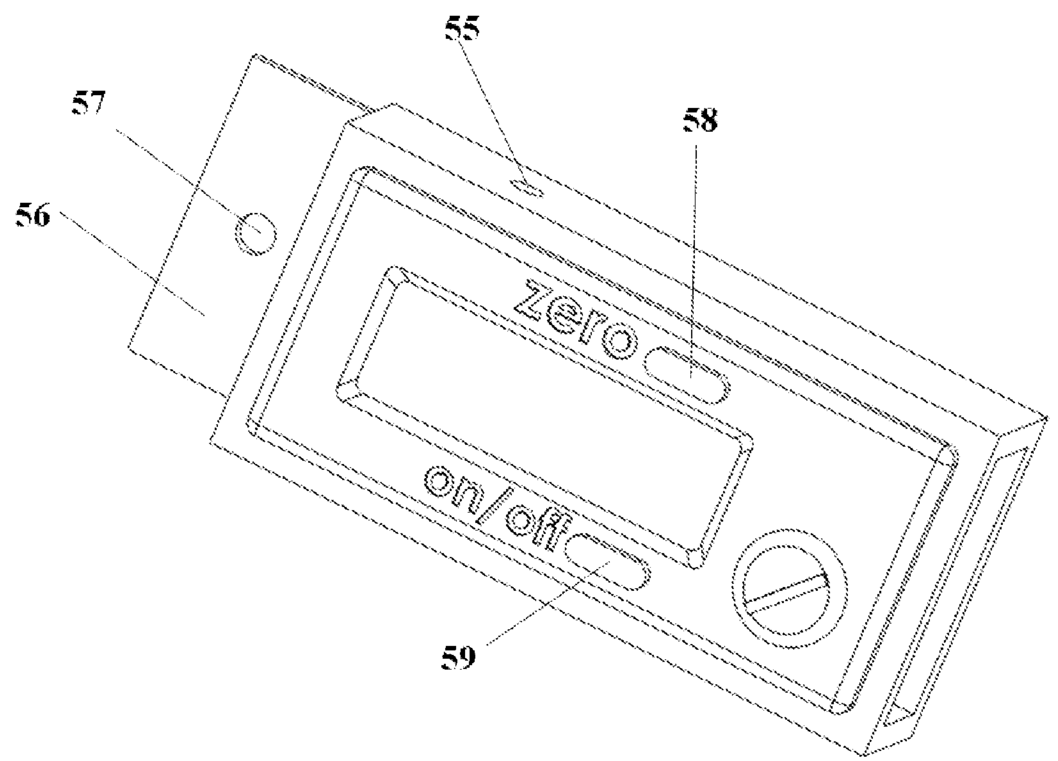
FIG. 12 is a schematic diagram of the digital display meter.

As shown in FIG. 12, the front part of the digital display meter 4 is provided with a connecting plate 56 which is protruding outward, the center of the connecting plate 56 is provided with a second through hole 57, and the surface of the digital display meter 4 is provided with a switch key 59 and a reset key 58, and the upper end of the digital display meter 4 is provided with a ninth threaded hole 55.

Figure 13:
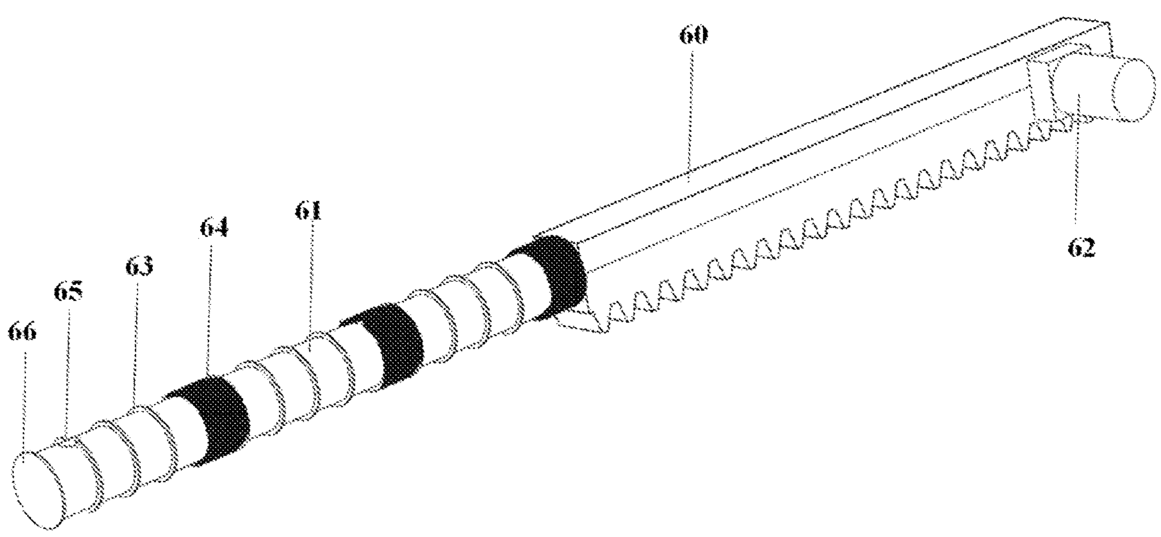
FIG. 13 is a schematic diagram of the depth measuring rod.

As shown in FIG. 13, the depth measuring rod 6 is integrally formed and can be divided into a first rack 60 and a cylindrical measuring head 61. The side wall of the first rack 60 is provided with a retaining rod 62 in a shape of a cylindrical protrusion. The retaining rod 62 passed through the hollow 15 and is exposed to the outer space of the first shell 1 when the assembly of the present device is completed. The optimal position of the retaining rod 62 is that enables the measuring head 61 to extend completely beyond the first shell 1 in the use state, and to exactly slide into the first shell 1 in the non-use state. Stable and reliable mechanical contacts with the starting end and the finishing end of the structure to be measured can be formed by the measuring head 61 or the two measuring claws.

The surface of the measuring head 61 is provided with a fine scale line 63 and a coarse scale line 64, and the distance between adjacent fine scale lines 63 is 1 mm. The width of the coarse scale line 64 is 1 mm, and the coarse scale lines 64 appear every 4 mm from the initial end of measuring head 66. The measuring head 61 is provided with a fifth threaded hole 65 with a distance of 1 mm between the axis of the fifth threaded hole 65 and the initial end of measuring head 66, and the axis of the fifth threaded hole 65 is perpendicular to the axis of the measuring head 61.

Figure 14:
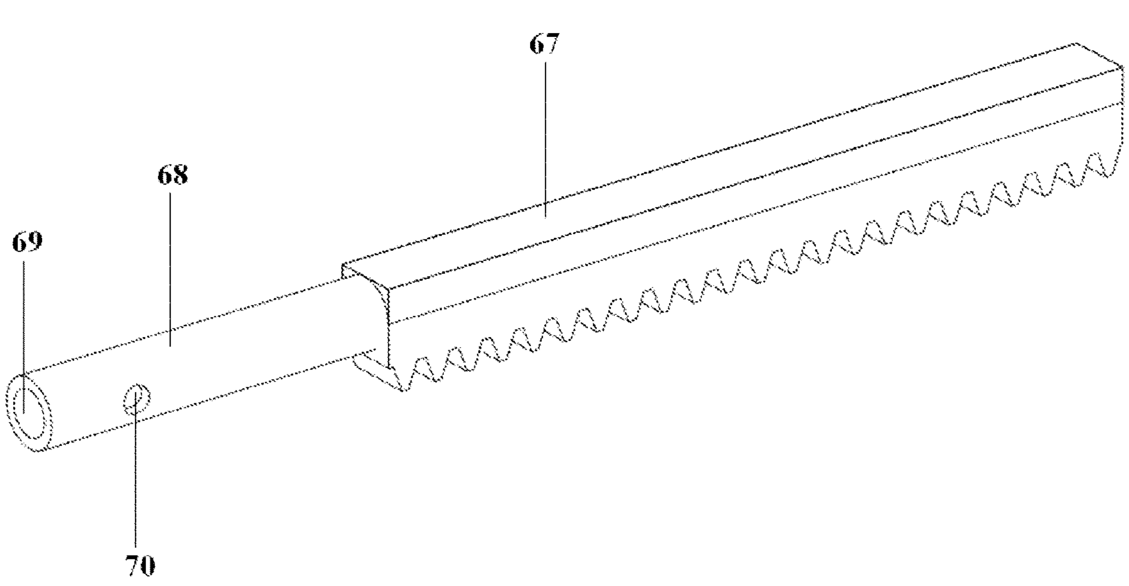
FIG. 14 is a schematic diagram of the transmission rod.

As shown in FIG. 14, the transmission rod 7 is integrally formed, and the transmission rod 7 is slidably installed in a second groove 30 of the second cover body 13. The transmission rod 7 consists of a second rack 67 and a protruding rod 68, the protruding rod 68 is cylindrical in shape. The specification of the second rack 67 is the same as that of the first rack 60, and the front end of the protruding rod 68 is provided with a second blind hole 69 and a tenth threaded hole 70, which are communicated with each other.

Figure 15:
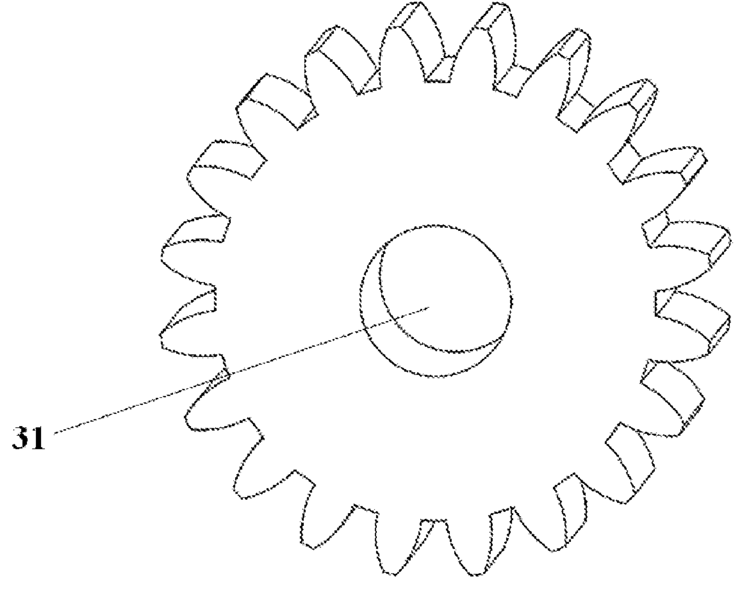
FIG. 15 is a schematic diagram of the gear.

As shown in FIG. 15, the thickness of the gear 8 is equal to the sum of the thicknesses of the first rack 60 and the second rack 67, and the center of the gear 8 is provided with a third shaft hole 31.

Figure 16:
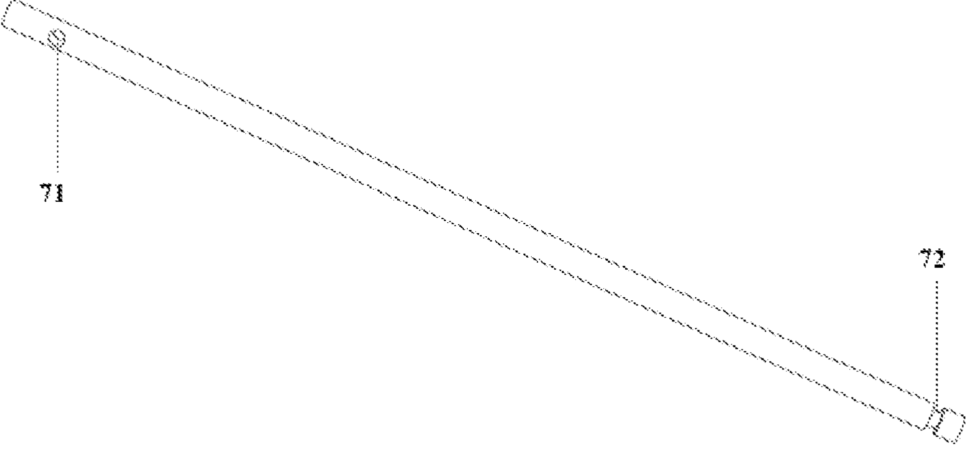
FIG. 16 is a schematic diagram of the connecting rod.

As shown in FIG. 16, the connecting rod 9 is of a long cylindrical structure, and one end of the connecting rod 9 is provided with a seventh through hole 71 and the other end of the connecting rod 9 is provided with a second annular groove 72.

Figure 17:
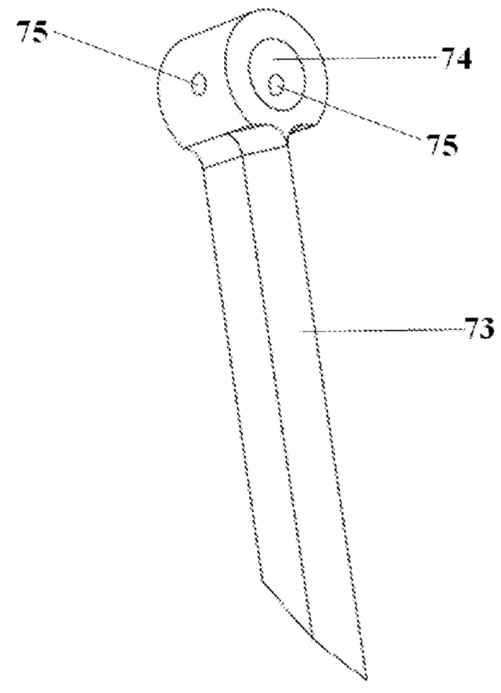
FIG. 17 is a schematic diagram of the first measuring claw.
Figure 18:
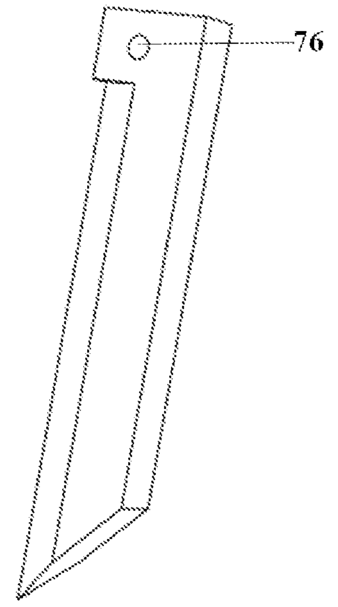
FIG. 18 is a schematic diagram of the second measuring claw.

As shown in FIGS. 17 and 18, the first measuring claw 10 consists of a blade and a third blind tube 74, the inner diameter of the third blind tube 74 is preferably closely matched with the measuring head 61, and the wall of the third blind tube 74 is penetrated by the third through hole 75. The axis of the third through hole 75 is perpendicular to the long axis of the third blind tube 74. The second measuring claw 11 is in the shape of a blade, and the end portion of the second measuring claw 11 is provided with a fourth through hole 76.

Embodiment 3

As shown in FIGS. 1 to 18, embodiment 3 is a specific use method proposed on the basis of embodiment 2:

Given value measurement method is used to check whether a certain distance dimension (including depth, height, length, width, etc.) reaches the due value of the certain distance, the specific measurement steps are as follows:

First of all, turning on the digital display meter 4, and deciding whether to install the measuring claw according to the characteristics of the distance to be checked, then performing the reset operation:

holding the digital display meter 4, and then pulling down the main scale 5, wherein the main scale 5 drives the connecting rod 9 and the transmission rod 7 to move downward together, at this time, the transmission rod 7 drives the gear 8 to rotate through the rack thereon, and because the gear 8 engages with the racks on the transmission rod 7 and the depth measuring rod 6 at the same time, the gear 8 drives the depth measuring rod 6 to move synchronously, so that the measuring head 61 is completely retracted into the first shell 1. The measuring head 61 can also be completely retracted into the first shell 1 by shifting the retaining rod 62 backward. And pressing the switch key 59 to turn on the digital display meter 4, and the screen of the digital display meter 4 shows zero.

Then, shifting the retaining rod 62 or pushing or pulling the main scale 5, making the display screen show the due value of the distance to be checked, then tightening the screw in the ninth threaded hole 55 of the digital display meter 4, so as to lock the relative position between the digital display meter 4 and the main scale 5, and starting the checking: making the head end of the measuring head 61 or the blade of the first measuring claw 10 contact with the starting point of the distance, and then checking whether the head end of the first shell 1 or the blade of the second measuring claw 11 is in contact with the stopping point of the distance, if so, it is proved that the distance dimension has reached the due value.

For example, when performing tooth preparation under guidance of depth-hole, this device can be used to check whether the depth-hole drilled on the tooth surface and used for guiding the amount of tooth preparation (grinding) has reached the expected depth through the above given value measurement method. The specific steps are as follows: first, adjusting the device to reach the expected depth, then tightening the screws in the ninth threaded hole 55 of the digital display meter 4, locking the relative position between the main scale 5 and the digital display meter 4, then inserting the measuring head 61 into the bottom of the depth-hole drilled on the tooth surface, and checking whether the head end of the first shell 1 is in contact with the tooth surface, wherein if the contact happens, it is proved that the depth has reached the required value.

When the measurement is completed, all the parts of the device can be disassembled, and the parts contacted with the patient's oral cavity should be sterilized and disinfected, so as to provide to the next patient for use.

Embodiment 4

As shown in FIGS. 1 to 18, embodiment 4 is a specific use mode proposed on the basis of embodiment 2:

When measuring the depth of the drilled hole, the height of the clinical crown and the preparation amount of the abutment teeth, the measuring claws are not installed. The specific measurement process is as follows:

First of all, performing the reset operation: holding the digital display meter 4, and then pulling down the main scale 5, wherein the main scale 5 drives the connecting rod 9 and the transmission rod 7 to move downward together, at this time, the transmission rod 7 drives the gear 8 to rotate through the rack thereon, and because the gear 8 engages with the racks on the transmission rod 7 and the depth measuring rod 6 at the same time, the gear 8 drives the depth measuring rod 6 to move synchronously, so that the measuring head 61 is completely retracted into the first shell 1. The measuring head 61 can also be completely retracted into the first shell 1 by shifting the retaining rod 62 backward. Then pressing the switch key 59 to turn on the digital display meter 4, and the screen of the digital display meter 4 shows zero.

When measuring the depth of the drilled hole or the height of the clinical crown, pressing the head end of the first shell 1 against the margin of the drilled hole or the incisal edge of the crown or the occlusal surface of the crown to be measured, then holding the digital display meter 4 by one hand and nudging the main scale 5 by the other hand. Wherein the main scale 5 drives the connecting rod 9 and the transmission rod 7 to move together, and the movement is synchronously transmitted to the depth measuring rod 6 through the gear 8, so that the measuring head 61 extends slowly until the measuring head 61 reaches the bottom of the drilled hole or the gingival margin of the apical side of the crown. At this time, rotating the digital display meter 4 to make the display screen of the digital display meter 4 convenient to observe, and then reading the value on the display screen directly, so that completing the measurement.

When the depth of the drilled hole to be measured is shallow or the crown is short, finely adjustment of the extending length of the measuring head 61 can be achieved by holding the digital display meter 4 by one hand and shifting the retaining rod 62 with tweezers by the other hand.

When measuring the preparation amount of the abutment teeth, the abutment preparation guide plate should be used. The specific measurement process is that: in the process of abutment preparation, placing the guide plate on the abutment teeth from time to time, and pressing the head end of the first shell 1 against the outer surface of the guide plate, shifting the retaining rod 62 with tweezers to make the measuring head 61 contact with the surface of the prepared abutment teeth, and then reading the value on the display screen.

Embodiment 5

As shown in FIGS. 1 to 18, embodiment 5 is a specific use mode proposed on the basis of embodiment 2:

When measuring the length and width of the oral anatomical structure the measuring claws need to be installed on the device, and the specific measuring steps are as follows:

Performing the reset operation in the first step: firstly, installing the first measuring claw 10 and the second measuring claw 11 to the corresponding positions of the measuring head 61 and the first shell 1 respectively, and securing them with screws; then holding the digital display meter 4 by one hand and pulling the main scale 5 by the other hand to retract the measuring rod into the first shell until the blades of the two measuring claws are tightly combined together;

then pressing the switch key to turn on the digital display meter 4; and then pressing the reset key 58, wherein the display screen shows zero.

Then holding the digital display meter 4 by one hand, and pushing the ruler body 51 with the other hand to make the measuring head 61 extend to the blades of the two measuring claws and contact with the beginning point and the stopping point of the distance to be measured on the measured structure, and then reading the value from the display screen.

For example, when measuring the width of a crown in the buccolingual direction, the width of the crown in the buccolingual direction can be read directly from the display screen by making the blades of the two measuring claws being contact with the buccal side and lingual side of the crown, respectively.

The aforementioned embodiments and examples further illustrate the purposes, technical solutions and beneficial effects of the present disclosure in detail. It is to be understood that the foregoing is only the embodiments of the present disclosure, and is not intended to limit the scope of the present disclosure. Any modifications, equivalent substitutes, improvements and the like made within the spirit and principle of the present disclosure should all be included in the scope of the present disclosure.

What is claimed is:

1. An oral cavity restoration space measuring device, comprising a shell, wherein the shell comprises: a combined section, the combined section comprises a transverse section and a longitudinal section, one end of the transverse section is a measuring end capable of extending into the oral cavity, and the longitudinal section and the transverse section are connected at an included angle, wherein the device further comprises a third shell, one end of the longitudinal section of the combined section away from the transverse section is connected with the third shell, and the longitudinal section is coaxial with the third shell, the combined section and the third shell are both cavity structures, an interior of the transverse section is provided with a depth measuring rod capable of extending to an outer space of the measuring end, and an interior of the longitudinal section is provided with a transmission rod;

the device further comprises a gear disposed at a connection position between the transverse section and the longitudinal section, the depth measuring rod and the transmission rod are capable of being engaged with the gear, and the transmission rod is slidable along an axis of the third shell and drive the gear, realizing the slide of the depth measuring rod in the transverse section under the driving of the gear, the device further comprises a connecting rod located inside the longitudinal section and the third shell, one end of the connecting rod is connected with one end of the transmission rod, and the other end of the connecting rod is connected with a main scale; by pushing or pulling the main scale, the connecting rod slides inside the longitudinal section and the third shell along the axis.

2. The oral cavity restoration space measuring device according to claim 1, wherein the longitudinal section is perpendicular to the transverse section.

3. The oral cavity restoration space measuring device according to claim 1, wherein an outer part of the main scale is sleeved with a digital display meter used for displaying measured data of the oral cavity restoration space, and the digital display meter is fixedly connected with the third shell.

4. The oral cavity restoration space measuring device according to claim 3, wherein the main scale is rotatable around an axis of the connecting rod.

5. The oral cavity restoration space measuring device according to claim 1, wherein the depth measuring rod comprises a first rack and a measuring head; a side wall of one end of the first rack is provided with a retaining rod, wherein the retaining rod extends out of the transverse section and is slidable in a hollow of the transverse section;

the measuring head is connected at the other end of the first rack away from the retaining rod, the measuring head can be extended and retracted along with the first rack, and the measuring head can be extended out of the transverse section and retracted into the interior of the transverse section.

6. The oral cavity restoration space measuring device according to claim 5, wherein the device further comprises a measuring assembly for performing dimension measurement, the measuring assembly comprises a first measuring claw and a second measuring claw, the first measuring claw is detachably connected at an end portion of the depth measuring rod extending out of the transverse section, the second measuring claw is detachably connected at an outer sidewall of one end of the transverse section, and a measuring gap is formed between the first measuring claw and the second measuring claw.

7. The oral cavity restoration space measuring device according to claim 3, wherein the depth measuring rod comprises a first rack and a measuring head; a side wall of one end of the first rack is provided with a retaining rod, wherein the retaining rod extends out of the transverse section and is slidable in a hollow of the transverse section;

the measuring head is connected at the other end of the first rack away from the retaining rod, the measuring head can be extended and retracted along with the first rack, and the measuring head can be extended out of the transverse section and retracted into the interior of the transverse section.

8. The oral cavity restoration space measuring device according to claim 7, wherein the device further comprises a measuring assembly for performing dimension measurement, the measuring assembly comprises a first measuring claw and a second measuring claw, the first measuring claw is detachably connected at an end portion of the depth measuring rod extending out of the transverse section, the second measuring claw is detachably connected at an outer sidewall of one end of the transverse section, and a measuring gap is formed between the first measuring claw and the second measuring claw.

* * * * *